(12) United States Patent
Matsumura

(10) Patent No.: US 8,068,902 B2
(45) Date of Patent: Nov. 29, 2011

(54) ELECTRODE DEVICE AND ELECTROCARDIOGRAPHIC MEASUREMENT DEVICE

(75) Inventor: Masafumi Matsumura, Neyagawa (JP)

(73) Assignee: Osaka Electro-Communication University, Osaka (JP)

(*) Notice: Subject to any disclaimer, the term of this patent is extended or adjusted under 35 U.S.C. 154(b) by 0 days.

(21) Appl. No.: 12/520,966

(22) PCT Filed: Dec. 25, 2006

(86) PCT No.: PCT/JP2006/325786
§ 371 (c)(1),
(2), (4) Date: Nov. 20, 2009

(87) PCT Pub. No.: WO2008/078380
PCT Pub. Date: Jul. 3, 2008

(65) Prior Publication Data
US 2010/0137726 A1    Jun. 3, 2010

(51) Int. Cl.
*A61B 5/0402* (2006.01)
(52) U.S. Cl. ...................................................... 600/509
(58) Field of Classification Search .......... 600/508–509, 600/382–392
See application file for complete search history.

(56) References Cited

U.S. PATENT DOCUMENTS

| | | | | | |
|---|---|---|---|---|---|
| 4,122,843 | A | * | 10/1978 | Zdrojkowski | 600/382 |
| 5,876,351 | A | * | 3/1999 | Rohde | 600/523 |
| 6,551,252 | B2 | * | 4/2003 | Sackner et al. | 600/536 |
| 2007/0078324 | A1 | * | 4/2007 | Wijisiriwardana | 600/386 |

FOREIGN PATENT DOCUMENTS

| | | |
|---|---|---|
| JP | 56-161036 | 12/1981 |
| JP | 9-56686 | 3/1997 |
| JP | 2003-325466 | 11/2003 |
| JP | 2003325466 | 11/2003 |

OTHER PUBLICATIONS

International Preliminary Report on Patentability issued in PCT/JP2006/325786 mailed Jul. 9, 2009 (with English translation).

* cited by examiner

*Primary Examiner* — Carl H Layno
*Assistant Examiner* — Paula J Stice
(74) *Attorney, Agent, or Firm* — Foley & Lardner LLP

(57) ABSTRACT

A device for electrocardiogram measurement is provided, which is relatively not easily influenced by electrical activities of muscles, and which can perform electrocardiogram measurement during a measured person's daily life without removing clothes. The device includes a pair of lead electrode sections that are provided on a band section. Each of the pair of lead electrode sections includes a lead electrode that is disposed so that the lead electrode is positioned in the vicinity of a carotid artery of the measured person when the band section surrounds a neck portion of the measured person. The band section is configured to include a flexible band, and the band section detachably holds onto the neck portion of the measured person with nipping force arising from elastic deformation of the flexible band.

6 Claims, 4 Drawing Sheets

(A)

(B)

ELECTRODE DEVICE AND ELECTROCARDIOGRAPHIC MEASUREMENT DEVICE

CROSS-REFERENCE TO RELATED APPLICATIONS

The present application is a U.S. national stage application claiming the benefit of International Application No. PCT/JP2006/325786, filed on Dec. 25, 2006, the entire content of which is incorporated herein by reference in its entirety.

TECHNICAL FIELD

The present invention relates to an electrode device and an electrocardiographic measurement device for measuring an electrocardiogram signal while being worn on a body of a measured person.

BACKGROUND ART

Hitherto, electrocardiogram measurement has been performed to be used in the diagnosis and treatment of heart diseases.

An electrocardiogram is a record of a state of electrical activities of a heart. Generally, standard 12-lead electrocardiography in which 12 types of waveforms are obtained using a combination of limb leads, the electrodes of which are placed on the four limbs, and chest leads, the electrodes of which are placed on a chest portion, is used for electrocardiogram measurement.

SUMMARY

Regarding the conventional method in which recording an electrocardiogram is performed with electrodes placed on the four limbs and a chest portion, there are problems given below.

More specifically, when electrodes are placed on the four limbs, movable portions such as arms and legs exist between the heart and the electrodes. Accordingly, electrical activities (electromyograms) of muscles of the movable portions tend to easily influence an electrocardiogram signal. In order to prevent noise that is caused by such electromyograms from being mixed in an electrocardiogram, the electrocardiogram needs to be measured in a resting state. Thus, regarding the method in which electrodes are placed on the four limbs, there is a problem that it is difficult to perform electrocardiogram measurement with a high accuracy during a measured person's daily life.

Furthermore, when electrodes are placed on a chest portion, the above-mentioned problem that is caused by the movable portions does not easily occur. However, on the other hand, clothes need to be removed when the electrodes are placed and removed. Regarding the method in which electrodes are placed on a chest portion, there is also a problem that the method is not necessarily suitable for electrocardiogram measurement during a measured person's daily life because the electrodes cannot be easily placed or removed while the measured person is wearing clothes.

Accordingly, it is an object of the present invention to provide an electrocardiogram measurement electrode device and an electrocardiographic measurement device that can perform electrocardiogram measurement during a measured person's daily life without removing clothes, and an electrocardiograph.

An electrocardiogram measurement electrode device according to the present invention includes a band section capable of surrounding a neck portion of a measured person; a reference electrode section that is provided on the band section, and that includes a reference electrode which is disposed so that the reference electrode is positioned in the vicinity of the vertebra prominens of the measured person when the band section surrounds the neck portion of the measured person; and a pair of lead electrode sections that are provided on the band section, each of the pair of lead electrode sections including a lead electrode, the lead electrode being disposed so that the lead electrode is positioned in the vicinity of a carotid artery of the measured person when the band section surrounds the neck portion of the measured person, and a voltage follower, an input terminal of the voltage follower being connected to the lead electrode, one of power-supply terminals of the voltage follower being connected to the reference electrode.

Preferably, the band section is configured to include a flexible band, and the band section detachably holds onto the neck portion of the measured person with nipping force arising from elastic deformation of the flexible band.

An electrocardiographic measurement device according to the present invention includes the electrocardiogram measurement electrode device according to the present invention; a differential amplifier that amplifies a difference between outputs of the respective voltage followers of the pair of lead electrode sections; and an electric circuit section that performs a filtering process on an output of the differential amplifier.

Preferably, the differential amplifier and the electric circuit section are mounted on the band section.

An electrocardiogram measurement electrode device according to the present invention includes a reference electrode section including a reference electrode; a pair of lead electrode sections, each of the pair of lead electrode sections including a lead electrode and a voltage follower, an input terminal of the voltage follower being connected to the lead electrode, one of power-supply terminals of the voltage follower being connected to the reference electrode; and a holding section that holds the reference electrode section so that the reference electrode is positioned in the vicinity of the vertebra prominens of a measured person, and that holds the pair of lead electrode sections so that the lead electrodes are positioned in the vicinities of carotid arteries of the measured person.

An electrocardiogram measurement method according to the present invention includes the following steps: detecting an electrocardiogram signal using a reference electrode that is disposed in the vicinity of the vertebra prominens of a measured person; detecting electrocardiogram signals using a pair of lead electrodes that are disposed in the vicinities of left and right carotid arteries of the measured person; inputting, in each of voltage followers disposed in the vicinity of a corresponding one of the lead electrodes, a corresponding one of the electrocardiogram signals that are detected using the lead electrodes which are disposed in the vicinities of the voltage followers to an input terminal, inputting the electrocardiogram signal that is detected using the reference electrode to one of power-supply terminals, and outputting an electrocardiogram signal; and taking, as inputs, the electrocardiogram signals that are output from the voltage followers, each of the voltage followers being disposed in the vicinity of a corresponding one of the lead electrodes, amplifying a difference between potentials of both of the signals, and outputting a bipolar lead electrocardiogram signal.

Features and a large number of advantages of the present invention will be properly evaluated when they are further understood by referring to the following detailed description and considering the accompanying drawings. Note that reference numerals are used to denote similar components through the entire description and the drawings unless stipulations of the reference numerals are provided.

According to the present invention, an electrocardiogram measurement electrode device and an electrocardiographic measurement device either of which is not easily influenced by an electromyogram and which can perform electrocardiogram measurement during a measured person's daily life without removing clothes can be provided.

Figure 1:
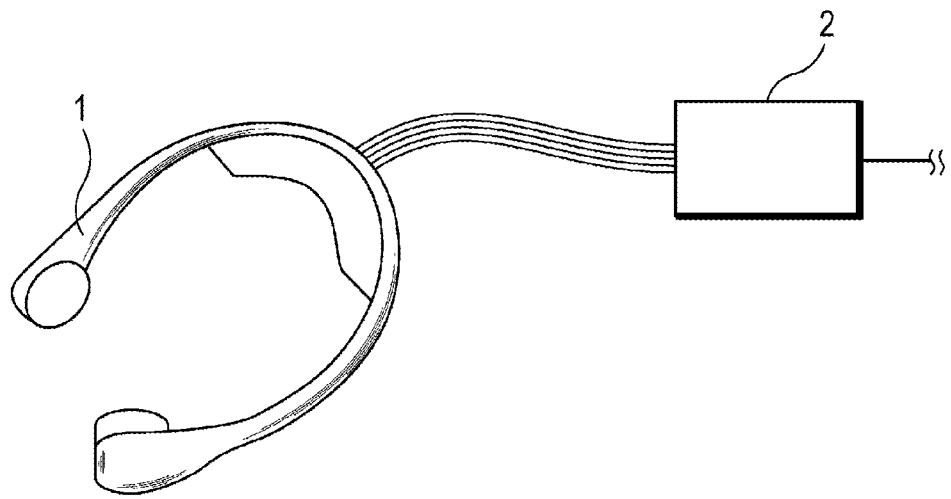
FIG. 1 is a diagram showing a schematic configuration of an electrocardiographic measurement device 100 according to an embodiment of the present invention.

| Reference Numerals | |
|---|---|
| 1 | electrocardiogram measurement electrode device |
| 2 | electrocardiogram signal processing device |
| 10 | flexible band section |
| 20 | reference electrode section |
| 21 | reference electrode |
| 22 | conductive fiber unit |
| 30 | lead electrode section |
| 31 | lead electrode |
| 32 | conductive fiber unit |
| 33 | voltage follower |
| 40 | differential amplifier |
| 50 | electric circuit section |
| 51 | high-pass filter |
| 52 | low-pass filter |
| 53 | band-rejection filter |

DETAILED DESCRIPTION

Embodiments of a method and device for monitoring a state of one's health through an electrocardiogram signal are described below. In the following description, a large number of detailed specific examples are used to provide thorough understanding of the embodiments of the present invention. However, persons skilled in the art can understand that the present invention can be realized even without some specific detailed portions or using other methods, elements, components, and so forth. In the other examples, commonly known configurations, components, operations are not shown in order to prevent the essence of the present invention from becoming unclear. Furthermore, the other examples are not described in detail.

In the entire specification, when description such as the term "an embodiment" is provided, it indicates that specific features, configurations, and characteristics which are described in relation to the embodiment are included in at least one embodiment of the present invention. Accordingly, an expression such as "in an embodiment" that is used in some sentences of the specification is not necessarily used to refer to the same embodiment. Furthermore, any combination of specific features, configurations, and characteristics can be preferably provided in one or more embodiments.

FIG. 1 is a diagram showing a schematic configuration of an electrocardiographic measurement device 100 according to an embodiment of the present invention. As shown in the figure, the electrocardiographic measurement device 100 includes an electrocardiogram measurement electrode device 1, an electrocardiogram signal processing device 2, and so forth. The electrocardiogram measurement electrode device 1 and the electrocardiogram signal processing device 2 are connected to each other via a plurality of lead wires.

Figure 2:
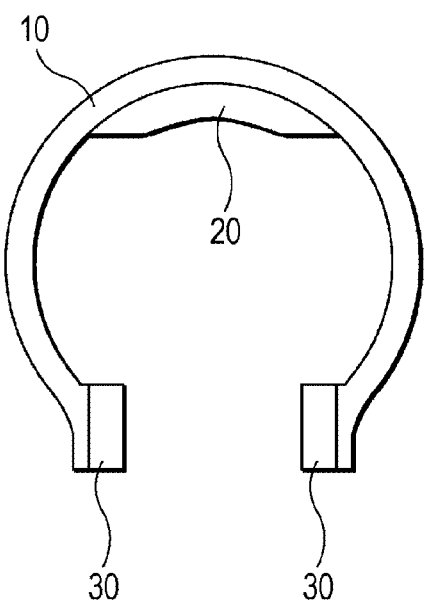
FIG. 2 is a diagram showing a configuration of an electrocardiogram measurement electrode device 1.

As shown in FIG. 2, the electrocardiogram measurement electrode device 1 includes a flexible band section 10, a reference electrode section 20 that is provided on the flexible band section 10, a pair of lead electrode sections 30 that are provided on the flexible band section 10, and so forth. The electrocardiogram measurement electrode device 1 is configured to be portable.

The flexible band section 10 has a so-called neck band shape allowing a neck portion of a measured person to be surrounded from the back side, and is formed of, for example, a plastic in an embodiment.

The flexible band section 10 can detachably hold onto the neck portion of the measured person with nipping force arising from elastic deformation of the flexible band section 10. However, when the electrocardiogram measurement electrode device 1 is worn, in addition to the nipping force, the flexible band section 10 is supported in the vicinity of the base of the neck portion of the measured person, whereby a wearing state is maintained.

Note that the flexible band section 10 may be configured to have a mechanism for adjusting a band length on an as-needed basis so that the band length can be available in various sizes of the periphery of the neck of the measured person (for example, a mechanism in which two or more bands are engaged so that the bands can slide into each other, such as a mechanism that is employed in conventional headphones or the like).

Figure 3:
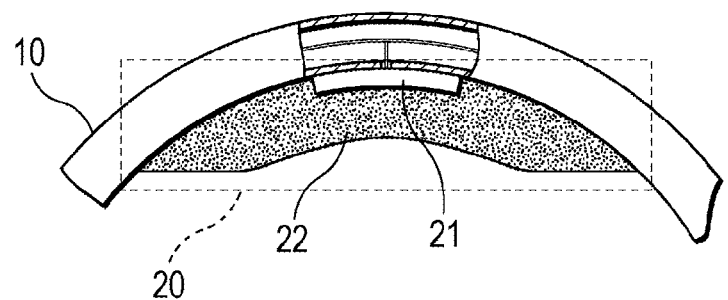
FIG. 3 is a diagram for explaining a reference electrode section 20 in an embodiment.

As shown in FIG. 3, the reference electrode section 20 is provided substantially at the center of the flexible band section 10. The reference electrode section 20 includes a reference electrode 21 that is disposed so that the reference electrode 21 is positioned in the vicinity of the vertebra prominens of the measured person when the measured person wears the electrocardiogram measurement electrode device 1 (i.e., when the flexible band section 10 surrounds the neck portion of the measured person); a conductive fiber unit 22 that is disposed so that the conductive fiber unit 22 is overlaid on the reference electrode 21, and that functions as a cushioning member between the reference electrode 21 and the neck portion of the measured person when the electrocardiogram measurement electrode device 1 is worn; and so forth (see FIG. 3).

The reference electrode 21 is formed, for example, of a carbon electrode having a circular shape with a diameter of 5 mm to 10 mm in an embodiment. When the electrocardiogram measurement electrode device 1 is worn, the reference electrode 21 indirectly contacts the vicinity of the vertebra prominens of the neck portion of the measured person via the conductive fiber unit 22, and is used to detect an electrocardiogram signal in the vicinity of the vertebra prominens of the neck portion. As described below, the reference electrode 21 is connected via lead wires to power-supply terminals of voltage followers 33 that are provided in lead electrode sections 30.

Note that the flexible band section 10, the reference electrode 21, and the conductive fiber unit 22 can be electrically connected to one another using one of various methods that are commonly known to persons skilled in the art. In an embodiment, the flexible band section 10, the reference electrode 21, and the conductive fiber unit 22 are bonded together using a conductive paste.

Figure 4:
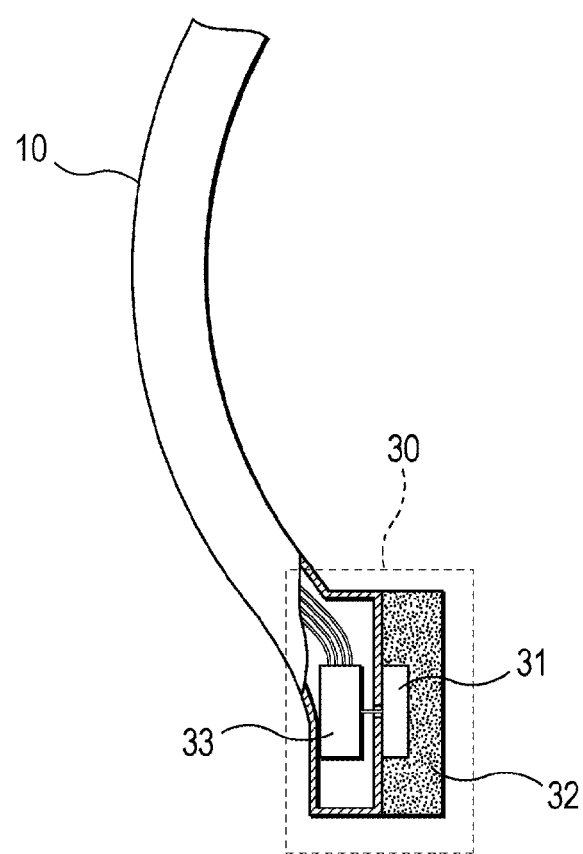
FIG. 4 is a diagram for explaining a lead electrode section 30 in an embodiment.

As described above, also as shown in FIG. 2, each of the pair of lead electrode sections 30 is provided at a corresponding one of ends of the flexible band section 10. The further details of the lead electrode section 30 in an embodiment are shown in FIG. 4. The lead electrode section 30 in the embodiment includes a lead electrode 31 that is disposed so that the lead electrode 31 is positioned in the vicinity of a carotid artery of the measured person when the measured person wears the electrocardiogram measurement electrode device 1; a conductive fiber unit 32 that is disposed so that it is overlaid on the lead electrode 31, and that functions as a cushioning member between the lead electrode 31 and the neck portion of the measured person when the electrocardiogram measurement electrode device 1 is worn; the voltage follower 33 which is disposed in the vicinity of the lead electrode 31 (for example, on the back side of the electrode 31 when it is regarded that the conductive fiber unit 32 is disposed on the front side of the lead electrode 31), an input terminal of which being connected to the lead electrode 31, one of power-supply terminals of which being connected to the reference electrode 21; and so forth. Note that the lead electrode 31 and the voltage follower 33 may be integrally shielded in a predetermined casing from which an electrode portion is exposed.

The lead electrode 31 can be formed, for example, of a carbon electrode having a circular shape with a diameter of 5 mm to 10 mm in an embodiment. When the electrocardiogram measurement electrode device 1 is worn, the lead electrode 31 indirectly contacts the vicinity of a carotid artery of the neck portion of the measured person via the conductive fiber unit 32, and is used to detect an electrocardiogram signal in the vicinity of the carotid artery of the neck portion.

Figure 5:
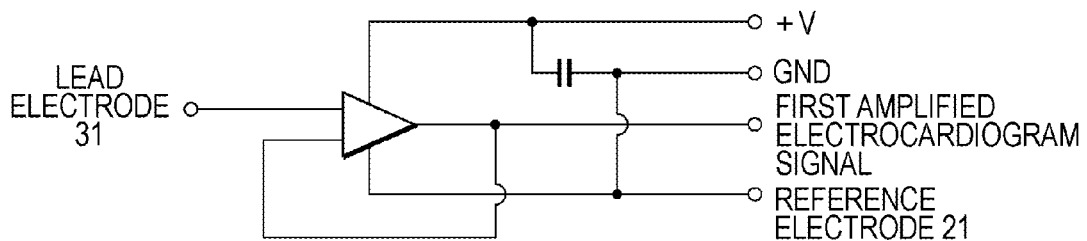
FIG. 5 is a diagram showing a circuit configuration of a voltage follower 33.

The voltage follower 33 takes, as an input, the electrocardiogram signal that is detected using the lead electrode 31, and outputs a first amplified electrocardiogram signal (see FIG. 5). Although the first amplified electrocardiogram signal is not substantially amplified, an output impedance of the electrocardiogram measurement electrode device 1 is converted into a low impedance by performing impedance conversion with the voltage follower 33. Note that it is preferable that an input impedance of the voltage follower 33 is set to be sufficiently high (for example, be equal to or higher than 2 MΩ).

Power is supplied to the power-supply terminals of the voltage follower 33 via lead wires from a power supply 60 that is provided in the electrocardiogram signal processing device 2. However, in order to cause the reference electrode 21 to function as an indifferent electrode, the lead wire from the reference electrode 21 is also connected to one of the power-supply terminals of the voltage follower 33, the one of power-supply terminals being connected to GND. The voltage follower 33 is configured so that a signal which is detected using the reference electrode 21 is input to the voltage follower 33. Accordingly, lead wires that are connected to the lead electrode section 30 (the voltage follower 33) include the lead wire from the reference electrode 21, the lead wire for outputting the first amplified electrocardiogram signal from the voltage follower 33, and the two lead wires for supplying power to the voltage follower 33, and the total number of lead wires is four.

Note that the flexible band section 10, the lead electrodes 31, and the conductive fiber units 32 can be bonded together, for example, using a conductive paste. Furthermore, the voltage followers 33 can be soldered on a predetermined substrate, and the substrate, for example, is bonded to the flexible band section 10 with an adhesive.

Figure 6:
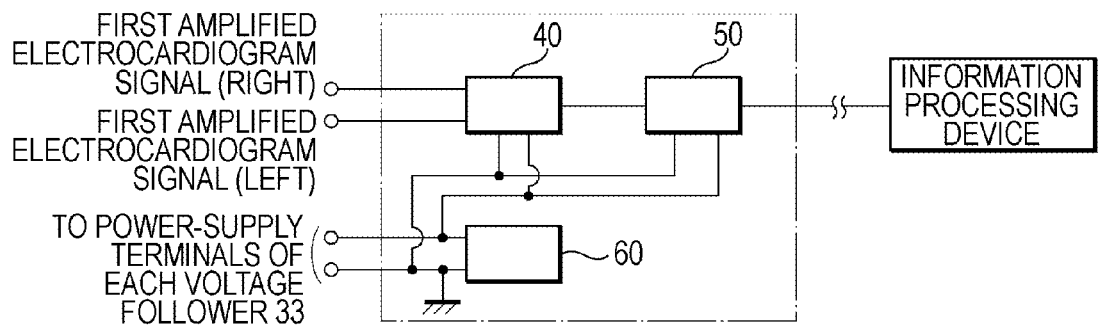
FIG. 6 is a diagram showing a configuration of an electrocardiogram signal processing device 2.

The electrocardiogram signal processing device 2 in an embodiment, as shown in FIG. 6, includes a differential amplifier 40 that takes the difference between outputs of the respective voltage followers 33 of the pair of lead electrode sections 30 as an input; an electric circuit section 50 that removes noise from an output of the differential amplifier 40 by performing a filtering process, and that outputs a signal; a power supply 60 that supplies power to each of the units; and so forth.

When the first amplified electrocardiogram signals that are output from the respective lead electrode sections 30 (the voltage followers 33) are input to two input terminals of the differential amplifier 40, the differential amplifier 40 amplifies the difference between potentials of both of the signals, and outputs a second amplified electrocardiogram signal (a bipolar lead electrocardiogram signal) from an output terminal.

Figure 7:
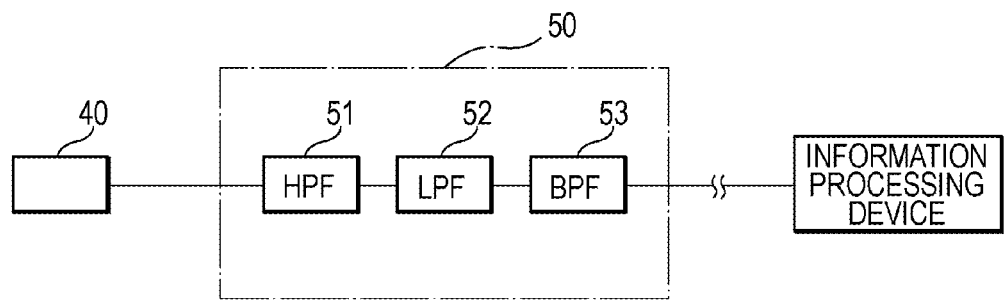
FIG. 7 is a diagram showing a configuration of an electric circuit section 50.

In an embodiment illustrated in FIG. 7, the electric circuit section 50 is configured to include filter circuits including a high-pass filter 51, a low-pass filter 52, and a band-rejection filter 53, and so forth.

When the second amplified electrocardiogram signal that is output from the differential amplifier 40 is input to the high-pass filter 51, the high-pass filter 51 outputs a third amplified electrocardiogram signal that is obtained by removing a direct current component from the second amplified electrocardiogram signal. When the third amplified electrocardiogram signal that is output from the high-pass filter 51 is input to the low-pass filter 52, the low-pass filter 52 outputs a fourth amplified electrocardiogram signal that is obtained by removing a high frequency component from the third amplified electrocardiogram signal. In the present embodiment, the high-pass filter 51 and the low-pass filter 52 are configured so that they cause signals having a bandwidth of 10 to 80 Hz to pass in order to accurately detect an R wave.

When the fourth amplified electrocardiogram signal that is output from the low-pass filter 52 is input to the band-rejection filter 53, the band-rejection filter 53 outputs a fifth amplified electrocardiogram signal that is obtained by removing lead noise associated with a commercial frequency of 50 Hz or 60 Hz from the fourth amplified electrocardiogram signal.

The fifth amplified electrocardiogram signal that is output from the electrocardiographic measurement device 100 (the electric circuit section 50 of the electrocardiogram signal processing device 2) is input to an information processing device for analyzing an electrocardiogram. In the information processing device, as in the conventional case, the fifth amplified electrocardiogram signal is converted into a digital signal by an A/D converter. After that, various types of analysis processes are performed on the digital signal by a microprocessor on an as-needed basis, and the digital signal or the result of analysis processes is displayed on a display device or recorded in a recording device.

Note that the power supply 60 supplies power to the differential amplifier 40, the electric circuit section 50, and so forth. In addition, the power supply 60 is connected to the electrocardiogram measurement electrode device 1 via the two lead wires, and supplies power to the voltage followers 33.

As described above, in the electrocardiographic measurement device 100 according to the present embodiment, since the electrocardiogram measurement electrode device 1 is provided as a neck-band-type device, electrocardiogram signals can be detected in the vicinities of the carotid arteries of a neck portion without constraining the four limbs and so forth. In the method in which electrocardiogram measurement is performed using electrodes placed on a neck portion, no portion having a large movable range, such as an arm or a leg, exists between the heart and the electrodes. Accordingly, even when electrocardiogram measurement is performed during a measured person's daily life, noise that is caused by electrical activities of muscles in the vicinities of the electrodes is markedly reduced using the method, compared with noise that occurs when the conventional scheme in which electrocardiogram measurement is performed using electrodes placed on the four limbs is used. Furthermore, because a neck portion is usually exposed, the electrocardiogram measurement electrode device 1 can be worn without removal of clothes, and electrocardiogram measurement can be performed. As a result, with the electrocardiographic measurement device 100 according to the present embodiment, electrocardiogram measurement can be performed almost without constraints to a measured person, without being invasive to the measured person, and further without causing the measured person to be aware that the measured person is wearing the electrocardiographic measurement device 100.

Furthermore, regarding the electrocardiographic measurement device 100 according to the present embodiment, the voltage followers 33 are provided in the lead electrode sections 30, thereby reducing noise. More specifically, when electrocardiogram signals are detected by electrodes placed on a neck portion, there is a constraint that it is difficult to use electrodes having a size as large as that of electrodes which is placed on the four limbs or a chest portion. Additionally, in the first place, when the size of each of the electrodes is increased, there is a risk that the electrodes interfere with movements of the neck portion, and the measured person also becomes increasingly annoyed. In contrast, when the size of each of the electrodes is reduced, the impedance of a signal source (the contact impedance of the electrode) increases, and a problem that noise immunity decreases occurs.

For this reason, in the present embodiment, although a constraint that the size of each of the electrodes is small is imposed when electrodes are placed on a neck portion, the voltage followers 33 are provided in the lead electrode sections 30 in order to satisfy the constraint and compensate for the decrease in noise immunity which is caused by the constraint. Since the electrocardiogram signals that are detected using the lead electrodes 31 are output from the electrocardiogram measurement electrode device 1 via the voltage followers 33, the output impedance of the electrocardiogram measurement electrode device 1 can decrease. As a result, noise immunity can be improved for the outputs of the electrocardiogram measurement electrode device 1. Furthermore, since each of the voltage followers 33 is disposed in the vicinity of a corresponding one of the lead electrodes 31, the distance between the voltage follower 33 and the lead electrode 31 can be reduced, whereby lead noise can be markedly reduced.

Figure 8:
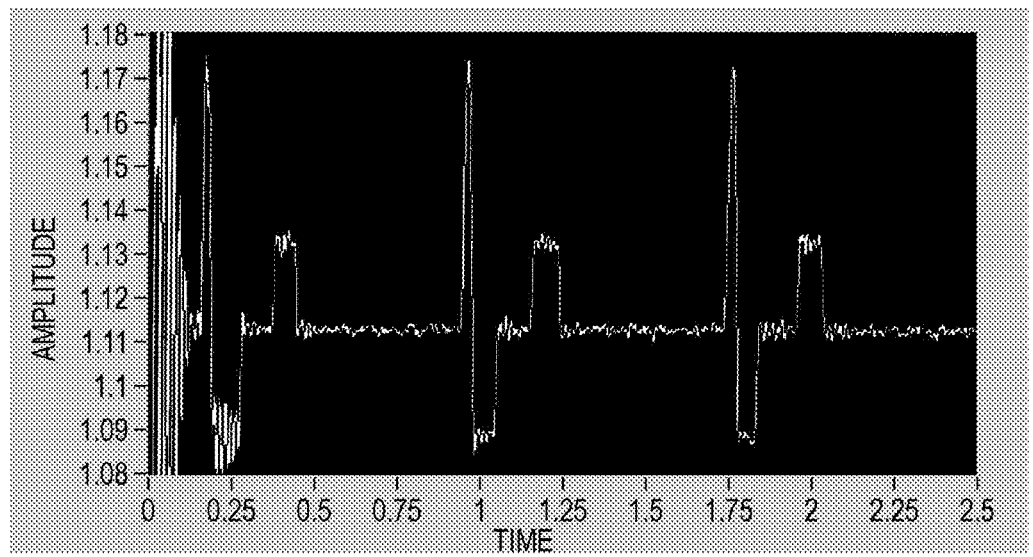
FIG. 8 includes graphs for explaining a fifth amplified electrocardiogram signal that is output from the electrocardiographic measurement device 100 and a comparison example.
Figure 8:
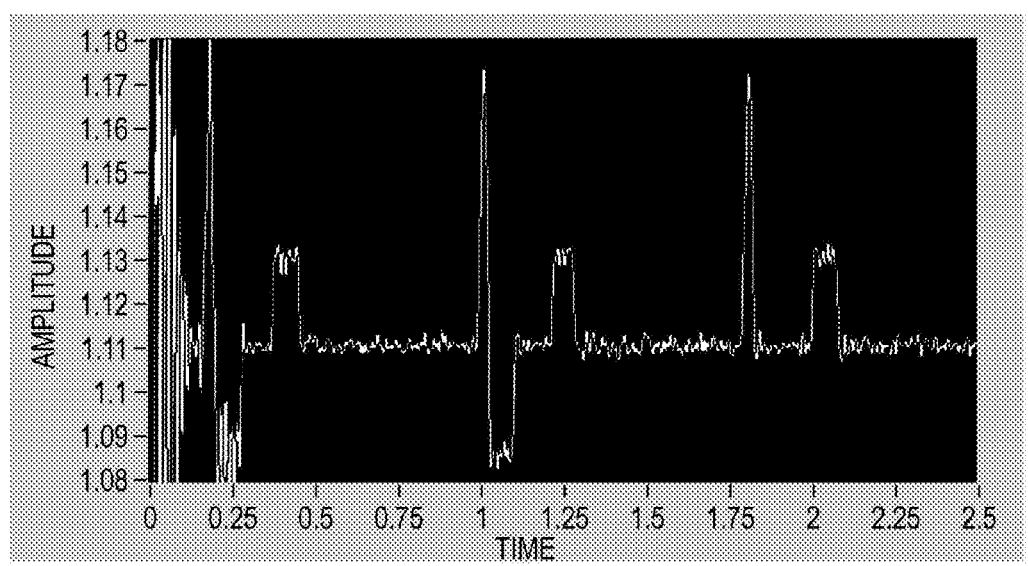

When the inventors of the present invention prototyped the electrocardiographic measurement device 100 according to the present embodiment, it was verified in reality that noise is reduced. In part (A) of FIG. 8, an example of the fifth amplified electrocardiogram signal that is output from the prototyped electrocardiographic measurement device 100 is shown. Additionally, in part (B) of FIG. 8, an example of the fifth amplified electrocardiogram signal in a comparison case is shown. In the comparison case, although a configuration that is substantially the same as the configuration of the electrocardiographic measurement device 100 is employed, an electrocardiogram signal that is detected using each of the lead electrodes 31 is directly input to the differential amplifier 40 without provision of a corresponding one of the voltage followers 33, and the second and higher-order amplified electrocardiogram signals are output. It can be understood that noise in the electrocardiogram signal shown in part (A) of FIG. 8, which is output from the electrocardiographic measurement device 100, is reduced, compared with noise in the electrocardiogram signal shown in part (B) of FIG. 8.

The present invention is not limited to the above-described embodiment, and various modifications can be made and applied. For example, although the electrocardiogram signal processing device 2 is formed as a device that is separated from the electrocardiogram measurement electrode device 1 in the above-described embodiment, both of the devices may be integrally formed by mounting the electrocardiogram signal processing device 2 on the flexible band section 10. Furthermore, a configuration may be used, in which some of or all of functions of the information processing device for analyzing an electrocardiogram are built in the electrocardiogram signal processing device 2.

Additionally, for example, a configuration in which the reference electrode section 20 and the lead electrode sections 30 are provided on the flexible band section 10 is used in the above-described embodiment. However, the configuration of the present invention is not necessarily limited to the above-described configuration. For example, a configuration may be used, in which the reference electrode section 20 and the lead electrode sections 30 are provided on an inflexible band section that is made of cloth or the like. In this case, for example, a configuration can be considered, in which hook and loop fasteners (referred to as "magic tape (registered trademark)") or the like are attached in the vicinities of both ends of the inflexible band section, and in which the inflexible band section is fixed using "magic tape (registered trademark)" or the like so that the inflexible band section surrounds the periphery of a neck portion of a measured person, thereby wearing the inflexible band section on the neck portion. Note that, in order to sufficiently ensure a function of holding the inflexible band section on a neck portion, it is preferable that the inflexible band section be formed using an extendable member.

Furthermore, for example, in the above-described embodiment, a configuration may be used, in which respective electrodes are held at appropriate positions on a neck portion using other mechanisms (for example, suction cups) instead of the flexible band section 10. Specifically, an electrocardiogram measurement electrode device is configured to include a reference electrode section including a reference electrode; a pair of lead electrode sections, each of the pair of lead electrode sections including a lead electrode and a voltage follower, an input terminal of the voltage follower being connected to the lead electrode, one of power-supply terminals of the voltage follower being connected to the reference electrode; and a holding section that holds the reference electrode section so that the reference electrode is positioned in the vicinity of the vertebra prominens of a measured person, and that holds the pair of lead electrode sections so that the lead electrodes are positioned in the vicinities of carotid arteries of the measured person.

Moreover, for example, a configuration may be used, in which the band section or the holding section can be attached to a collar portion of a shirt or the like. Alternatively, a configuration can be considered, in which the collar portion of a shirt or the like is used as the band section or the holding section. With this configuration, a so-called wearable electrocardiogram measurement electrode device and a so-called wearable electrocardiographic measurement device can be realized.

Furthermore, for example, in the above-described embodiment, a configuration is used, in which the electric circuit section 50 includes the high-pass filter, the low-pass filter, and the band-rejection filter. However, a configuration may be used, in which the electric circuit section 50 includes a different filter (for example, a low-emphasis filter or a band-pass filter) in addition to/instead of the filters.

Additionally, for example, in the above-described embodiment, a configuration is used, in which signals are output from the electrocardiogram measurement electrode device 1 to the electrocardiogram signal processing device 2 via the lead wires, and in which a signal is also output from the electrocardiogram signal processing device 2 to the outside via a lead wire. However, a configuration may be used, in which each of the electrocardiogram measurement electrode device 1 and the electrocardiogram signal processing device 2 outputs a signal using wireless. Specifically, the electrocardiogram measurement electrode device 1 or/and the electrocardiogram signal processing device 2 are each configured to include a transmitter and an antenna. After an electrocardiogram signal is subjected to a modulation process by the transmitter, the electrocardiogram signal is transmitted as an electric wave from the antenna to a device that is an output destination.

The invention claimed is:

1. An electrocardiogram measurement electrode device comprising:
   a band section configured to partially surround a neck portion of a measured person;
   a reference electrode section that is provided on the band section, and that includes a reference electrode configured to be positioned in a vicinity of the vertebra prominens of the measured person when the band section surrounds the neck portion of the measured person; and
   a pair of lead electrode sections that are provided on the band section, each of the pair of lead electrode sections including:
   (i) a lead electrode configured to be positioned in a vicinity of a carotid artery of the measured person when the band section surrounds the neck portion of the measured person, and
   (ii) a voltage follower, wherein an input terminal of the voltage follower is connected to the lead electrode, and a power-supply terminal of the voltage follower is connected to the reference electrode.

2. The electrocardiogram measurement electrode device according to claim 1, wherein the band section includes a flexible band, and the band section is configured to detachably hold onto the neck portion of the measured person with a force arising from elastic deformation of the flexible band.

3. An electrocardiographic measurement device comprising:
   the electrocardiogram measurement electrode device according to claim 1 or 2;
   a differential amplifier configured to amplify a difference between outputs of the respective voltage followers of the pair of lead electrode sections; and
   an electric circuit section configured to perform a filtering process on an output of the differential amplifier.

4. The electrocardiograph according to claim 3, wherein the differential amplifier and the electric circuit section are mounted on the band section.

5. An electrocardiogram measurement electrode device comprising:
   a reference electrode section including a reference electrode;
   a pair of lead electrode sections, each of the pair of lead electrode sections including:
   (i) a lead electrode, and
   (ii) a voltage follower, wherein an input terminal of the voltage follower is connected to the lead electrode and one power-supply terminal of the voltage follower is connected to the reference electrode; and
   a holding section configured to hold the reference electrode section in a vicinity of the vertebra prominens of a measured person, and configured to hold the pair of lead electrode sections in vicinities of carotid arteries of the measured person.

6. A method for detecting an electrocardiogram signal, the method comprising the steps of:
   detecting an electrocardiogram signal using a reference electrode that is disposed in a vicinity of the vertebra prominens of a measured person;
   detecting electrocardiogram signals using a pair of lead electrodes that are disposed in respective lead electrode sections each placed in vicinities of left and right carotid arteries respectively, of the measured person;
   inputting, through a respective voltage followers each disposed in corresponding the respective lead electrode sections, a corresponding one of the electrocardiogram signals that are detected using the lead electrodes to an input terminal, inputting the electrocardiogram signal that is detected using the reference electrode to one of power-supply terminals, and outputting an electrocardiogram signal; and
   taking, as inputs, the electrocardiogram signals that are output from the voltage followers, each of the voltage followers being disposed in the vicinity of a corresponding one of the lead electrodes, amplifying a difference between potentials of both of the signals, and outputting a bipolar lead electrocardiogram signal.

* * * * *